United States Patent
Berggren

(10) Patent No.: US 7,079,914 B2
(45) Date of Patent: Jul. 18, 2006

(54) SYSTEM AND METHOD FOR PRODUCING A THREE-DIMENSIONAL BODY COMPRISING BONE OR TISSUE-COMPATIBLE MATERIAL

(75) Inventor: Carina Berggren, Torslanda (SE)

(73) Assignee: Nobel Biocare AB, Göteborg (SE)

( * ) Notice: Subject to any disclaimer, the term of this patent is extended or adjusted under 35 U.S.C. 154(b) by 0 days.

(21) Appl. No.: 10/710,221

(22) Filed: Jun. 28, 2004

(65) Prior Publication Data

US 2005/0154483 A1    Jul. 14, 2005

Related U.S. Application Data

(63) Continuation of application No. PCT/SE02/02384, filed on Dec. 19, 2002.

(30) Foreign Application Priority Data

Dec. 28, 2001  (SE) .................................... 0104447

(51) Int. Cl.
*G06F 19/00*  (2006.01)
*G05B 19/18*  (2006.01)

(52) U.S. Cl. ........................... 700/119; 700/212; 700/60

(58) Field of Classification Search ................. 700/60, 700/61, 62, 118, 119, 180, 182, 185, 196, 700/197, 212
See application file for complete search history.

(56) References Cited

U.S. PATENT DOCUMENTS

| | | | |
|---|---|---|---|
| 4,104,798 A * | 8/1978 | Takahashi et al. ....... | 433/222.1 |
| 4,575,805 A | 3/1986 | Moermann et al. | |
| 4,837,732 A | 6/1989 | Brandestini et al. | |
| 5,121,329 A * | 6/1992 | Crump ...................... | 700/119 |
| 5,510,066 A * | 4/1996 | Fink et al. ................. | 264/40.1 |
| 5,938,446 A | 8/1999 | Andersson et al. | |
| 5,993,731 A * | 11/1999 | Jech et al. ..................... | 419/19 |
| 6,506,217 B1 | 1/2003 | Arnett | |
| 6,730,129 B1 | 5/2004 | Hall | |
| 2002/0072821 A1* | 6/2002 | Baker .......................... | 700/98 |

FOREIGN PATENT DOCUMENTS

| | | |
|---|---|---|
| WO | WO 9515731 | 6/1995 |
| WO | WO 9637163 | 11/1996 |
| WO | WO 9814628 | 4/1998 |
| WO | WO 9844864 | 10/1998 |
| WO | WO 9962422 | 12/1999 |
| WO | WO 03061509 | 7/2003 |

* cited by examiner

*Primary Examiner*—Leo Picard
*Assistant Examiner*—Sean Shechtman
(74) *Attorney, Agent, or Firm*—Connolly Bove Lodge & Hutz LLP; Larry J. Hume

(57) ABSTRACT

A system useful in producing a three-dimensional body comprising bone or tissue-compatible material includes a detection and analysis site which identifies and simulates a portion of a body in connection with an implantation situation. A production device produces a model responsive to the simulation information. A flame-spraying apparatus provides the bone-compatible and/or tissue-compatible material in a powder form through a nozzle. Relative movement between the nozzle and a support member supporting the model or die is controlled to apply one or more layers of the bone-compatible material to the model. A method includes using a computer to identify and simulate a body in connection with a given implantation situation, and producing a model or die accordingly. the bone or tissue-compatible material is flame-sprayed in a powder form. Movements of a nozzle and/or a supporting member are controlled so as to effect a desired surface characteristic on the three-dimensional body.

17 Claims, 1 Drawing Sheet

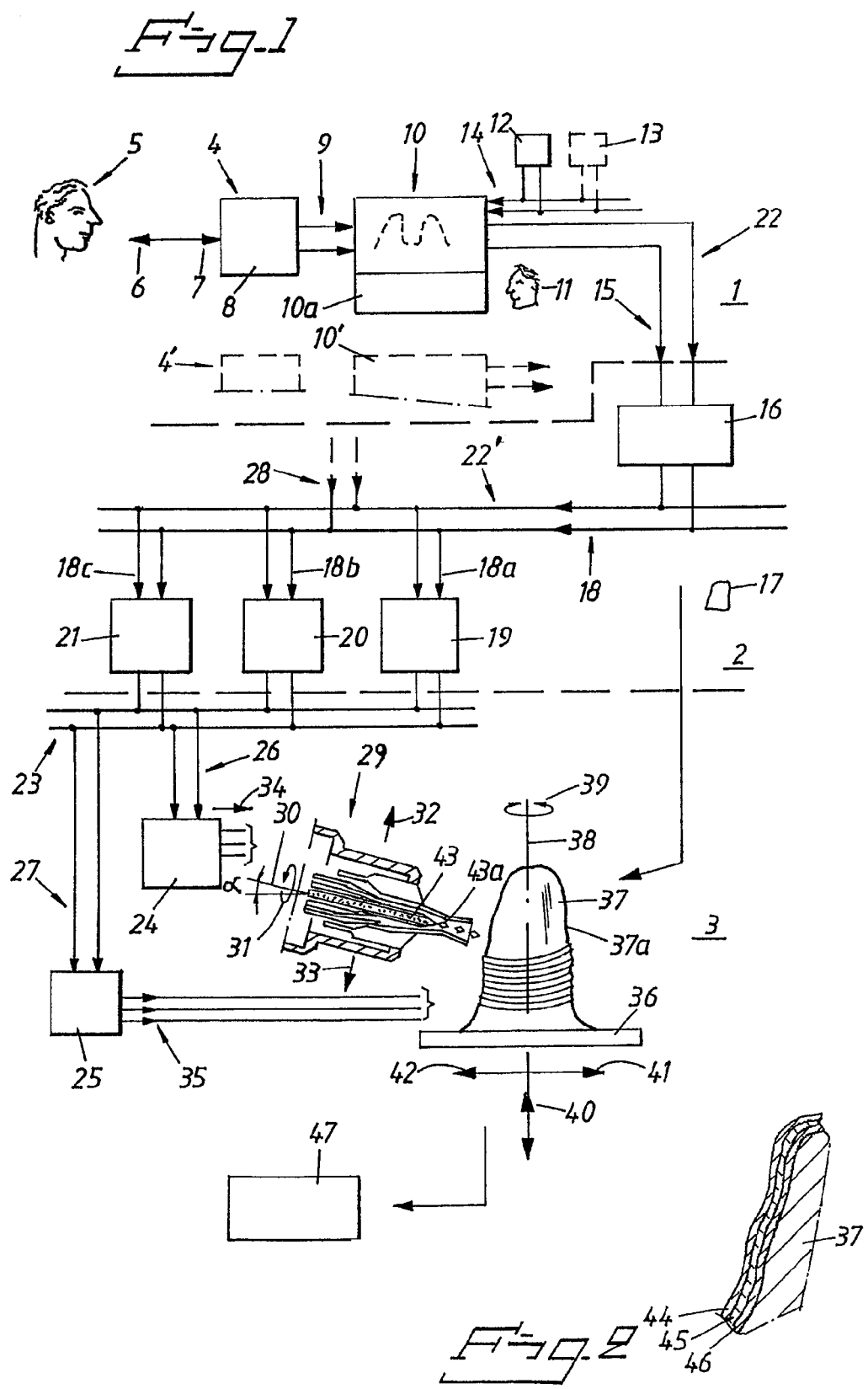

SYSTEM AND METHOD FOR PRODUCING A THREE-DIMENSIONAL BODY COMPRISING BONE OR TISSUE-COMPATIBLE MATERIAL

CROSS REFERENCE TO RELATED APPLICATIONS

This application is a continuation under 35 U.S.C. §120 of co-pending International Application PCT/SE02/02384 filed Dec. 19, 2002. PCT/SE02/02384 claims priority to Swedish Application SE 0104447-8 filed Dec. 28, 2001. The entire contents of each of PCT/SE02/02384 and SE 0104447-8 are incorporated herein by reference.

BACKGROUND OF THE INVENTION

This disclosure relates to an arrangement for producing a three-dimensional body made of bone-compatible and/or tissue-compatible material, preferably meaning titanium in this case. This disclosure also relates to a device in the form of a three-dimensional body made of bone-compatible and/or tissue-compatible material, and to a use of such a body.

It is known to produce three-dimensional bodies (dental crowns, implants, etc.) with the aid of a scanned implantation situation, simulation function, model production etc., and to control the production of the body or product from a blank which is machined, for example mechanically and/or electrochemically, in order to produce the final product.

Thus, for example, it is proposed to use support members which can be controlled in rotation and in the vertical direction relative to a scanner and function member. The scanning can be done optically or mechanically, with camera equipment, etc. It is also known to use computed tomography in connection with an analysis function which is carried out with the aid of computer equipment, in which the respective implantation situation can be simulated and analyzed together with the detected and desired product.

A High Velocity Oxygen Fuel (HVOF) thermal flame spraying process using powder is also used conventionally to coat pump axles, piston rods, rotor axles, rollers, etc., with layers of desired materials. Such apparatus can use oxygen gas and a combustible gas or liquid which, under high pressure, are driven into a combustion chamber where the gases are mixed and atomized. When the mixture is combusted, the pressure increases very rapidly and the gas can flow out from the chamber. The powder is introduced into the hot jet stream and also accelerates very quickly to supersonic speed. The out flowing molten powder material forms the layer or layers. The flame temperatures can be about 2800° C., and the particle velocity can be about 800 m/s.

In production of three-dimensional bodies, for example dental crowns, implants, etc., there is a need for new arrangements and methods previously used in the field to be improved or replaced from the point of view of efficiency and economics, while maintaining or enhancing the required production precision and effectiveness. In the production of products in a dental context, individually adapted products must be produced which are to be made in one or more copies, which further increases the requirements in terms of cost and efficiency. It is desired that the new principles of production are able to employ existing aids in connection with the use. Thus, for example, it is desired that the new arrangements can be included in and used together with computer-based aids, computed tomography, X-rays, modern scanning aids, etc.

BRIEF SUMMARY OF THE INVENTION

In one embodiment, an arrangement includes a computer-based first apparatus to identify and simulate the body in connection with a given implantation situation. It also includes a second apparatus for producing a model or die as a function of the identification or simulation. A unit for high-velocity flame spraying of material in powder form via a nozzle and movement-controlling members for controlling the nozzle and members supporting a model or the die is disclosed. In other aspects, the unit may be arranged to apply coating layers to the model or die via the nozzle during simultaneous movement control of the nozzle and/or the supporting members. The layer coating can be controlled or emanate from the first apparatus and/or the second apparatus to form the body.

In further developments of the inventive concept, variations in the wall thickness and outer configurations can be effected by means of control of the high-velocity flame and/or the mutual movements between nozzle and body.

An apparatus of an embodiment comprises a number of layers situated on one another and applied by high-velocity flame spraying of the material in powder form. The layers in the hardened state are preferably self-supporting from the point of view of strength.

In another embodiment, an apparatus for high-velocity flame spraying of the material in powder form is used in order to apply layers to the die or model during movement of a nozzle in the apparatus and/or the die or the model or a member supporting this.

In one embodiment, a system useful in producing a three-dimensional body comprising bone or tissue-compatible material includes a detection and analysis site which identifies and simulates a portion of a body in connection with an implantation situation. A production device produces a model responsive to the simulation information. A flame-spraying apparatus provides the bone-compatible and/or tissue-compatible material in a powder form through a nozzle. Relative movement between the nozzle and a support member supporting the model or die is controlled to apply one or more layers of the bone-compatible material to the model.

In another embodiment, a method includes using a computer to identify and simulate a body in connection with a given implantation situation, and producing a model or die accordingly the bone or tissue-compatible material is flame-sprayed in a powder form. Movements of a nozzle and/or a supporting member are controlled so as to effect a desired surface characteristic on the three-dimensional body.

In another embodiment, a method includes using a computer to identify and simulate a body in connection with a given implantation situation, and producing a model or die accordingly. Thereafter the bone or tissue-compatible material is flame-sprayed in a powder form. Movements of a nozzle and/or a supporting member are controlled so as to of effect a desired surface characteristic on the three-dimensional body.

By means of what has been proposed above, a new way is found of producing three-dimensional products for dentistry and/or for the human body, or blanks for such products. The model or die is coated with thin layers of molten titanium powder which are applied on top of one another until the desired body shape has been obtained. With the layers in the hardened state, the body can be removed from the die and, in one embodiment, can be used directly.

BRIEF DESCRIPTION OF THE DRAWINGS

Embodiments of an apparatus, a. device, and a use will be described below with reference to the attached drawings in which:

FIG. 1 shows, diagrammatically and in block form, an arrangement for producing a body, or a blank for a body, by means of high-pressure flame spraying, preferably of titanium powder; and FIG. 2 shows, in a greatly enlarged view, a number of layers which are arranged on a die or model and which have been applied to it by means of the high-pressure flame spraying.

DETAILED DESCRIPTION

In FIG. 1, a first apparatus is indicated by 1, a second apparatus is indicated by 2, and a third apparatus is indicated by 3. The interfaces between the apparatus can be arranged in different suitable ways. The first apparatus, which can be conventionally known, comprises scanning equipment 4 which is used to determine a dental situation on a patient 5. The scanning function can be conventional, and the determination of the implantation situation in question can thus be effected with the aid of a model, by optical scanning and imaging by means of a camera, for example. The imaging is represented by an arrow 6, and the result obtained from the imaging, indicated by an arrow 7, is delivered to equipment 8 which detects the imaging and is of the type which can convert the image to digital information, which is represented by 9. In a computer appliance 10, the digital information 9 can be received and an analysis can be performed by a user 11 in interaction between the user and the computer appliance. The computer appliance can be provided with control elements 10a, speech-activated control members, etc., by means of which the user performs the analysis work. The analysis function can also include help functions such as computed tomography carried out with equipment 12 provided for this purpose or library 13 which contain empirical information. Information from such external sources 12, 13 has been indicated by 14 in FIG. 1.

The analysis function by means of the apparatus 1 can result in an information transmission signal 15 which is intended for a production unit 16 included in the apparatus 2. The production unit can serve a number of detection and analysis sites in accordance with the above, and a further set of the apparatus in question has been indicated by 4' and 10'. The different first apparatuses can be sited at different dentists, dental technicians, etc. The produced template or die can be transferred manually, for example by post, transport, etc. Alternatively, information signals 18 (files) can be transmitted to transmission units 19, 20, 21, etc., which are each assigned their own function or their information/files.

The production unit 16 may be connected to the first apparatus via a first bus connection 22, and the units 19, 20, 21 may be connected to the production unit 16 via a second bus connection 22'. The units 19, 20 and 21 may also be connected to an outward bus connection, here designated as third bus connection 23. First and second control units 24 and 25 may also be connected to bus connection 23.

File information 18 on the second bus connection 22' can be divided up into different information parts or files 18a, 18b and 18c. The control units 24 and 25 can take in control information from one or more of units 19, 20 and 21, and the control unit 24 is thus able to receive information or file 26, and the control unit 25 is able to receive information or file 27.

The last-mentioned information/files 26 and 27 can emanate directly from the first apparatus 1, as has been indicated by broken lines 28. Information/files 26 and 27 relate to control functions or control data for an apparatus for high-velocity flame spraying of powder, to which the control unit 24 is connected or forms part of in a conventional manner.

As a function of the control information 26, control unit 24 can control a nozzle 29 forming part of apparatus 3. The control can effect rotational or tilting movements about or of its longitudinal axis 30. The rotation movement is indicated by 31, and the tilting movement by $\alpha$.

Alternatively, or in addition to this, nozzle 29 can also be displaced in parallel in the directions of the arrows 32 and 33, and in directions in toward and out from the plane of FIG. 1. The actuation function from the control unit 24 is shown by an arrow 34.

Correspondingly, by means of control signals 35, the control unit can act on a support member 36 for a model or die 37. The support member/model/die can thus be rotated about a vertical axis 38, the rotation arrows having been indicated by 39. The member 36 and model/die 37 may also be displaced in the vertical direction 40, and side directions 41, 42.

The information or file 27 and the control signals 35 issuing from control unit 25 can also relate to the structure of the model or die, which applies in cases where the produced model is to be transmitted by electrical information/files. The information can alternatively be transmitted on diskettes.

As regards the function of the apparatus for high-velocity flame spraying, this will not be described in detail here, because conventional equipment may be used.

As indicated in FIG. 1, nozzle 29 comprises an air cap and channels for compressed air, oxygen, propane, or oxygen-hydrogen. There is also a central channel for the powder material 43 which is, in one embodiment, titanium powder applied with the aid of a carrier gas comprising, e.g., nitrogen. Nozzle 29 thus comprises inner and outer nozzles for the above components. Information signals 34 provided to the nozzle can also include information on the quantities of the various components and the powder, the flame temperature, the particle velocities, etc.

Depending on the controlled flame-spraying function and movement function, molten particles 43a are directed toward the outer surface 37a of the model/die 37 or to layers which have already been sprayed onto this surface. In accordance with one aspect of this disclosure, nozzle 29 and model/die 37 execute mutual or coordinated movements as a function of the controls, during which molten powder 43a included in a high-velocity flame coats the surface 37a which is moving relative to it. In this way, layers can gradually be built up on surface 37a.

In accordance with another aspect of this embodiment, multiple layers located on top of one another may be applied to surface 37a.

FIG. 2 shows, in a greatly enlarged view, three layers 44, 45 and 46 arranged on top of one another on model/die 37.

When the layers have hardened, the body thus formed by the layers 44, 45, 46, etc., may be removed from the model or die 37. It may be removed in a conventional manner, and this is represented by 47 in FIG. 1.

In accordance with the above, a body (blank) is obtained which is self-supporting from the point of view of strength, and which can be used for dental products or for other products for the human body. By means of control signals 34 and 35, body 47 can be structured with very great precision, which is important in a dental context in connection with dental crowns, spacers, for example.

Third apparatus 3 can be controlled in such a way as to give the desired outer configuration directly which, in certain situations, means that body 47 does not have to undergo any further after-treatment. Body 47 thus acquires good properties from the point of view of precision and strength.

By means of this disclosure, it is thus possible to use equipment for high-velocity flame spraying of powder, made from bone-compatible and/or tissue-compatible material, simultaneously with a movement function in accordance with the above. As an alternative to titanium powder, it is possible to use powder made from gold alloy, steel, etc. In the case of titanium powder, pure powder (99.99%) with relatively small particles, for example Wah Chang HP (or CP)-325 Mesh T0800I4(010607), may be used.

Communication bus connections may be known data and/or telecommunication links, which may include or comprise public networks, i.e., the Internet, for example.

Model or template 37 may be produced in production unit 16 or at another site which receives production information from the unit 16, see FIG. 1.

This disclosure is not limited to the embodiments described above, and instead it can be modified within the scope of the attached patent claims and the inventive concept.

The invention claimed is:

1. An apparatus useful in producing a three-dimensional dental product comprising bone-compatible and/or tissue-compatible material, the apparatus comprising:
   identification and simulation means for identifying and simulating at least a portion of a dental crown or implant in connection with a dental implantation situation;
   a production device which produces a dental model or die responsive to identification and simulation information provided by the identification and simulation means;
   a flame-spraying apparatus which provides the bone-compatible and/or tissue-compatible material in a powder form through a nozzle; and
   means for controlling movement between the nozzle and a support member supporting the dental model or die, wherein the flame-spraying apparatus is arranged to apply layers of the bone-compatible and/or tissue-compatible material to the dental model or die via the nozzle during simultaneous movement control of at least one of the nozzle and the supporting member.

2. A system useful in producing a three-dimensional dental product comprising bone-compatible and/or tissue-compatible material, the system comprising:
   a detection and analysis site comprising identification and simulation means for identifying and simulating at least a portion of a dental crown or implant in connection with a dental implantation situation;
   a production device which produces a dental model or die responsive to identification and simulation information provided by the identification and simulation means;
   a flame-spraying apparatus which provides the bone-compatible and/or tissue-compatible material in a powder form through a nozzle; and
   means for controlling movement between the nozzle and a support member supporting the dental model or die, wherein the flame-spraying apparatus is arranged to apply a layer of the bone-compatible and/or tissue-compatible material to the dental model or die via the nozzle while simultaneously controlling movement between the nozzle and the supporting member.

3. The system of claim 2, wherein the bone-compatible and/or tissue-compatible material comprises titanium.

4. The system of claim 2, wherein the identification and simulation means comprises a computer processor.

5. The system of claim 2, further comprising means for controlling a surface configuration of the three-dimensional dental product.

6. The system of claim 2, wherein variations in a wall thickness of the bone-compatible and/or tissue-compatible material covering the dental model or die are controlled by means for controlling one or both of the flame-spray apparatus and the movement between the nozzle and the dental model or die.

7. The system of claim 2, wherein plural thin layers of the bone-compatible and/or tissue-compatible material are applied to the dental model or die from the nozzle, wherein the plural thin layers form a framework.

8. The system of claim 7, wherein the framework on the three-dimensional dental product is suitable for being separated from the dental model or die after the plural layers have hardened.

9. The system of claim 3, wherein the titanium comprises titanium powder having a purity of 99.99%.

10. The system of claim 3, wherein the titanium comprises titanium powder having a small-particle size of 325 mesh.

11. The system of claim 2, further comprising plural detection and analysis sites separated from each other, wherein the production device produces multiple dental models responsive to associated identification and simulation information provided by respective ones or the plural detection and analysis sites.

12. The system of claim 2, further comprising a communication network which couples the identification and simulation information to the detection and analysis site.

13. A three-dimensional dental product produced by the system of claim 2, wherein the three-dimensional dental product is suitable for use in an implantation process.

14. A method for producing a three-dimensional dental product comprising bone-compatible and/or tissue-compatible material, the method comprising:
   using a computer to identify and simulate a dental crown or implant in connection with a given dental implantation situation;
   producing a dental model or die responsive to the identification and simulation of the dental crown or implant;
   flame-spraying the bone-compatible and/or tissue-compatible material in a powder form through a nozzle;
   applying one or more coating layers of the bone-compatible and/or tissue-compatible material to the dental model or die via the nozzle; and
   simultaneously, with said applying one or more coating layers, controlling movement of die nozzle and/or a supporting member of the dental product so as to effect a desired surface characteristic on the three-dimensional dental product.

15. The method of claim 14, wherein the bone-compatible and/or tissue-compatible material comprises titanium powder.

16. The method of claim 14, further comprising:
   hardening the one or more coating layers of the bone-compatible and/or tissue-compatible material;
   removing the three-dimensional dental product from the dental model or die; and
   using the three-dimensional dental product in the given dental implantation situation.

17. A three-dimensional dental product produced by the method of claim 14.

* * * * *